(12) United States Patent
Taeubert et al.

(10) Patent No.: US 8,380,322 B2
(45) Date of Patent: Feb. 19, 2013

(54) ELECTRODE DEVICE FOR ACTIVE MEDICAL IMPLANTS

(75) Inventors: Kerstin Taeubert, Berlin (DE); Hartmut Lenski, Glienicke (DE); Ingo Weiss, Berlin (DE); Michael Friedrich, Kleinmachnow (DE); Stefan Knorr, Berlin (DE); René Fischer, Berlin (DE); Marc Steffen Schurr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 169 days.

(21) Appl. No.: 13/018,454

(22) Filed: Feb. 1, 2011

(65) Prior Publication Data

US 2011/0196463 A1   Aug. 11, 2011

(30) Foreign Application Priority Data

| Feb. 11, 2010 | (DE) | ................ 10 2010 000 367 |
| Feb. 11, 2010 | (DE) | ................ 10 2010 000 369 |
| Feb. 11, 2010 | (DE) | ................ 10 2010 000 370 |
| Feb. 11, 2010 | (DE) | ................ 10 2010 000 371 |
| Feb. 11, 2010 | (DE) | ................ 10 2010 000 372 |

(51) Int. Cl.
*A61N 1/00* (2006.01)
(52) U.S. Cl. ........................................ 607/115
(58) Field of Classification Search ........... 607/115, 607/63, 116; 606/41; 333/175; 29/825
See application file for complete search history.

(56) References Cited

U.S. PATENT DOCUMENTS

| 7,363,090 | B2 | 4/2008 | Halperin |
| 2009/0281592 | A1 | 11/2009 | Vase |
| 2010/0016936 | A1 | 1/2010 | Stevenson et al. |
| 2010/0217262 | A1* | 8/2010 | Stevenson et al. ............. 606/41 |
| 2010/0231327 | A1* | 9/2010 | Johnson et al. ............... 333/175 |
| 2011/0034979 | A1* | 2/2011 | Min et al. ...................... 607/116 |

FOREIGN PATENT DOCUMENTS

EP   2025361 A1   2/2009

OTHER PUBLICATIONS

European Search Report dated May 6, 2011 (7 pages).

* cited by examiner

*Primary Examiner* — George Manuel
*Assistant Examiner* — Robert N Wieland
(74) *Attorney, Agent, or Firm* — ARC IP Law, PC; Joseph J. Mayo

(57) ABSTRACT

Electrode device for active medical implants with an elongated electrode body (2) having a proximal end and a distal end (1), a tip contact pole (6) on the distal end (1), at least one ring contact pole (5) before the distal end (1), electrical supply leads (3, 4) to the tip and ring contact pole (6, 5), and a high-frequency filter (11) before the distal end (1), which has electrical contact to the tip contact pole (6) and is connected to the supply lead (4) thereof.

20 Claims, 11 Drawing Sheets

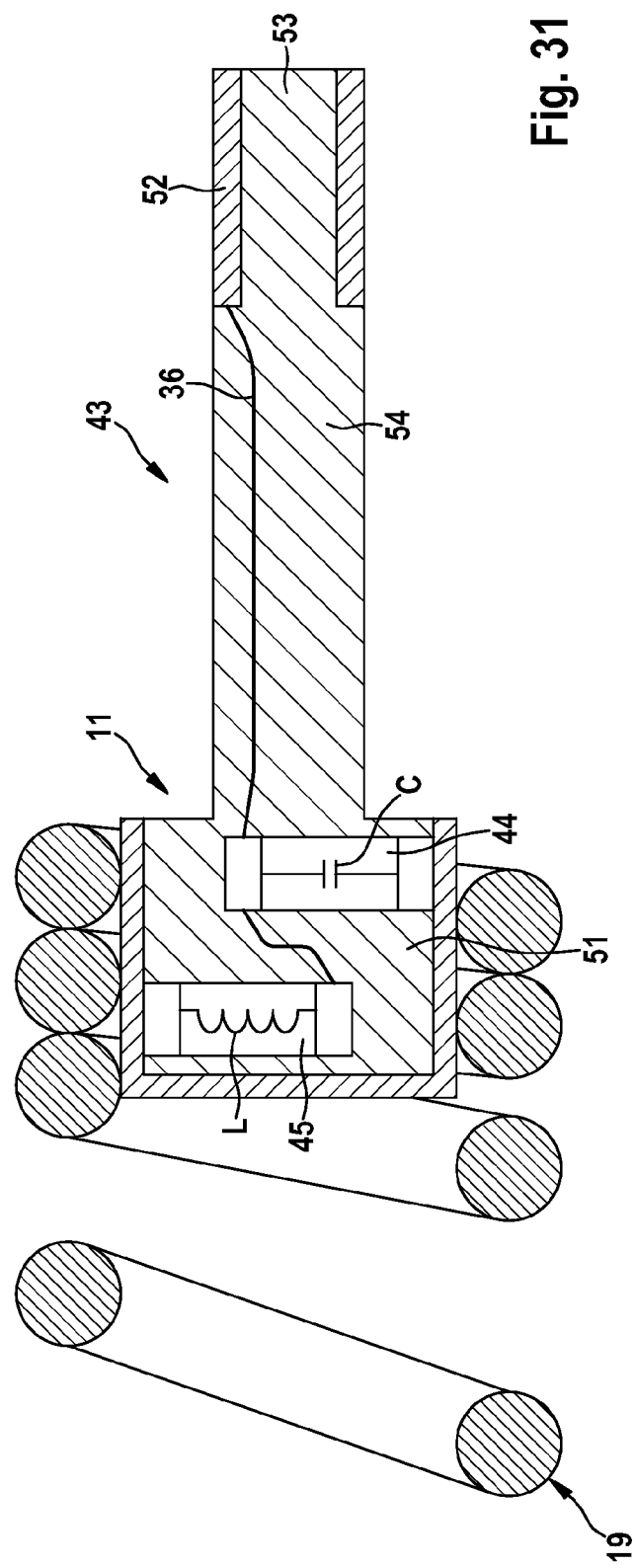

ELECTRODE DEVICE FOR ACTIVE MEDICAL IMPLANTS

This application takes priority from German Patent Application DE 10 2010 000 367.0, filed 11 Feb. 2010, German Patent Application DE 10 2010 000 369.7, filed 11 Feb. 2010, German Patent Application DE 10 2010 000 370.0, filed 11 Feb. 2010, German Patent Application DE 10 2010 000 371.9, filed 11 Feb. 2010, German Patent Application DE 10 2010 000 372.7, filed 11 Feb. 2010, the specifications of which are all hereby incorporated herein by reference.

BACKGROUND OF THE INVENTION

1. Field of the Invention

The invention relates to an electrode device for active medical implants.

2. Description of the Related Art

The background of the invention is that the subject matter of the invention is relevant primarily in conjunction with cardiac pacemakers, implantable defibrillators, and other types of active implantable electromedical devices. The latter typically comprise at least one current/voltage-carrying supply lead in the electrode device—which is typically referred to simply as an "electrode"—, the distal end of which is located e.g. in a ventricle and is used to measure cardiological potential signals or to transmit relevant therapeutic current signals.

In the case of implantable electromedical devices, the compatibility of such electrode devices with high-frequency magnetic fields of the type used in imaging diagnostic methods in particular which are based on magnetic resonance—so-called MRI (magnetic resonance imaging) methods—is a serious problem. In such MRI methods, a magnetic alternating field pulsed with radio frequency (RF) is superimposed on a strong static magnetic field, the former being used to change the energy state of the protons in the tissue being investigated and produce MRI signals from the tissue.

Due to the laws of electromagnetic induction, this magnetic alternating field induces alternating voltages in the supply lead of the electrode devices—under discussion here—of electromedical device implants; the energy of the alternating voltages is converted to heat in particular at the electrically conductive contact poles of the electrode device with human tissue. This can result in considerable heating e.g. of the tip contact of a cardiac electrode, thereby impairing or even damaging the surrounding cardiac tissue or cardiac tissue in contact therewith.

To prevent these problems, U.S. Pat. No. 7,363,090 B2 proposes the use of filters on the basis of oscillating circuits composed of a coil in parallel with a capacitor, which is assigned to the corresponding supply lead for the tip contact pole or a ring contact pole of a corresponding electrode of an implantable electromedical device. The filters disclosed in this known patent are designed in practical application by the patent owner as relatively bulky components that reinforce the electrode device along a certain length and impart unfavorable mechanical properties to the electrode equipped therewith. Furthermore, the filter is accommodated in a closed housing that does not provide passage for the guide wires that are typically used when implanting an electrode. The potential uses of this known electrode having a filter device are therefore limited.

US 2009/0281592 A1 makes known filtering components for reducing heating of pacemaker electrodes of an electromedical implant caused by the effect of high-frequency magnetic fields produced during MRI procedures, in which case an induction coil is provided around a non-conductive central portion of a shaft that interconnects a tip contact pole to an inner coil conductor of the electrode device. By mounting an induction coil on the shaft, inductive signal filtering can be provided so as to reduce electrode tip heating, without requiring the incorporation of a lengthy, bulky inductor along the length of the electrode. Capacitive elements can also be integrated in the shaft to create an LC filter circuit. As an alternative thereto, a so-called "air coil" is disclosed in this publication as an inductive element, in which case the shaft can be omitted.

The filter devices according to the prior art typically result in excessive stiffening of the electrode device along a certain length.

BRIEF SUMMARY OF THE INVENTION

Proceeding therefrom, the problem addressed is that of improving electrode devices for active medical implants such that the electrode body is made as flexible as possible due to advantageous installation positions of the high-frequency filter.

This problem is solved by the features of an electrode device as claimed herein, which comprises:
- an elongated electrode body having a proximal end and a distal end,
- a tip contact pole on the distal end,
- at least one ring contact pole before the distal end,
- electrical supply leads to the tip contact pole and the ring contact pole, and
- a high-frequency filter before the distal end, which has electrical contact with the tip contact pole and is connected in the supply lead thereof.

Due to the design of an electrode device according to the invention, various specifications regarding the flexibility of the electrode device can be implemented depending on the objective of the particular electrode device. For example, by positioning the high-frequency filter and the contact pole relative to one another such that they overlap radially at least partially, it is possible to position the tip contact pole and the ring contact pole more or less close to one another and simultaneously incorporate the high-frequency filter, thereby making it possible to obtain a short pole distance between tip and ring while ensuring that the design is compact.

Advantageously, in the case of such a partial overlap, the spiral supply lead for the ring contact pole can terminate in front of the high-frequency filter in the proximal direction. In the axial direction, the high-frequency filter and the supply lead are therefore offset axially, thereby making it possible to create an electrode body that is thinner overall. Therefore, it is no longer necessary to accommodate the supply lead itself between the high-frequency filter and the ring electrode.

A connection of the ring contact pole and the high-frequency filter having an efficient circuit design is given when the outer supply lead for the ring contact pole simultaneously has electrical contact with the outer housing surface of the high-frequency filter. In turn, this housing surface is electrically coupled to the corresponding filter components in the housing interior.

The diameter of the electrode body can be minimized further according to a preferred embodiment in which the ring contact pole is disposed in front of the high-frequency filter in the proximal direction such that the ring contact pole and the high-frequency filter do not overlap axially. The inner diameter of the ring contact pole, possibly including the spiral supply lead thereof, is smaller than the outer diameter of the high-frequency filter. According to this embodiment, the filter and the ring pole are therefore separated completely in the axial direction in terms of their positioning, and so, in the extreme case, the outer diameter of the high-frequency filter, possibly including insulation, can correspond to the outer diameter of the ring electrode.

The flexibility of the electrode device in the region of the tip is improved according to a further preferred embodiment by mechanically and electrically connecting the high-frequency filter to the tip contact pole using a flexible spiral piece. The spiral piece therefore performs a dual function as an electrical supply lead and a mechanical joint, thereby ensuring that no noteworthy losses of flexibility will occur due to the connection of the tip contact pole to the high-frequency filter given an appropriately flexible, insulating design of the electrode body in this region.

According to further preferred variants of the invention, the tip contact pole can be a head comprising an electrically active fixing screw, a lenticular, conical, or hemispherical head, an elongated contact pin which is designed as a fixing screw, of the high-frequency filter, or an extension of the housing of the high-frequency filter. Clearly, therefore, the invention opens up distinctly variable ways to implement the tip contact pole.

A feature of a development of the subject of the invention is to incorporate the high-frequency filter into the mechanical rotary drive of a tip contact pole designed as an electrically active fixing screw. As a result, the high-frequency filter is supported together with the tip contact pole in the electrode device, in particular inside the ring contact pole, such that it can rotate about the longitudinal axis of the electrode device. For this purpose, bearing washers having bores are preferably provided in the electrode device, in which the high-frequency filter and the contact pins thereof are rotatably supported, and by way of which the electrical supply lead of the tip contact pole is driven in a rotational manner. The result is easy rotatability and an operator-friendly way of attaching the tip contact pole of the electrode device at the site of diagnosis/therapy.

According to a further preferred embodiment, the high-frequency filter comprises electrical contact pins having miniature electronic components connected therebetween, the contact pins and the miniature components being situated together in a bonded manner in an enclosing filter housing applied by injection molding. This filter embodiment makes it possible to design the filter to be compact, mechanically robust, and insulated in an electrically clean manner, thereby making it particularly suitable for installation in the electrode device.

The filter housing can be adapted in an optimal manner to the particular conditions for use by applying a functional coating e.g. in the form of a vapor barrier or a ceramic or metallic coating.

The further development of the electrode device according to the invention is also used for this purpose; according thereto, the contact pins are each designed as tubes, the lumen of which align with a passage in the filter housing through which a guide wire extends for implantation of the electrode device. The capability of the electrode device to be introduced is therefore improved since a guide wire can be used despite the integrated high-frequency filter.

Another aspect of one or more embodiments of the invention also relates to the housing design of the high-frequency filter, the contact pins of which can be designed as contact caps that are insulated against one another and face one another with the edges thereof. A type of barrel filter is therefore created, in the interior of which the electrical filter components are housed. Advantageous electrical connections of these components to the contact caps include sliding contacts or contact springs between the connectors of the electrical components and the interior of the contact caps.

Finally, it is possible to integrate the high-frequency filter directly in the tip contact pole, which also ensures that the flexibility of the electrode body will not be reduced.

Furthermore it is possible to use the described technology in catheters, especially ablation catheters.

In addition to the embodiments described herein other alternative embodiments may include some or all of the disclosed features.

BRIEF DESCRIPTION OF THE DRAWINGS

Further features, details, and advantage of the invention will be apparent from the description of embodiments that follows, with reference to the attached drawings. In the drawings:

FIGS. 22 to 31 show schematic coaxial longitudinal sectional views of tip contact poles having integrated high-frequency filters in different embodiments.

DETAILED DESCRIPTION OF THE INVENTION

Figure 1:
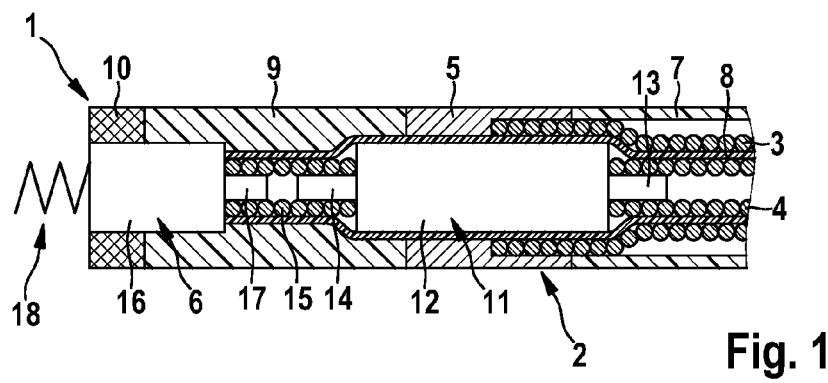
FIGS. 1 to 5 show coaxial longitudinal sectional views of an electrode device in the distal end region thereof, in different embodiments.

The basic design of an electrode device of the type used e.g. as a pacemaker electrode of an implantable cardiac pacemaker will be explained with reference to FIG. 1. If the descriptions of the further embodiments according to FIGS. 2 to 31 do not relate to contrary embodiments, then the corresponding explanations also apply for these embodiments, and identical reference characters label similar components and therefore do not need to be explained in detail once more.

FIG. 1 shows the region before distal end 1 of the electrode device, with which an elongated electrode body 2 is terminated. Extending therein are two spiral supply leads 3, 4, i.e. an outer supply lead 3 to a ring electrode 5 disposed before distal end 1, and an inner supply lead 4 which is used for the electrical connection of tip contact pole 6 on distal end 1 of the electrode device in a manner to be explained in greater detail.

Electrode body 2 is closed on the outside by an insulating tube 7. An insulation layer 8 which is likewise tubular is located between supply leads 3, 4. A flexible insulation sleeve 9 which is terminated by a steroid collar 10 is placed between ring contact pole 5 and tip contact pole 6.

An aspect common to the embodiments according to FIGS. 1 to 5 is that a high-frequency filter 11 is installed in the region before distal end 1 of the electrode device. This filter, which is designed as an LC oscillating circuit and is composed e.g. of a coil having inductance L and a capacitor having capacitance C, is used to filter out the initially mentioned high-frequency currents induced by the magnetic field in MRI systems. Heating of ring contact pole 5 and, in particular, tip contact pole 6 is thereby effectively prevented. In the embodiments according to FIGS. 1 to 5, high-frequency filter 11 is shown as a uniform component having a cylindrical housing 12 and connectors 13, 14 disposed coaxially toward the proximal side and the distal side on the housing end faces.

In the embodiment according to FIG. 1, ring contact pole 5 is situated approximately in the center and therefore overlaps the high-frequency filter completely in the axial direction, wherein insulation layer 8 has been drawn between ring contact pole 5 and filter 11 for electrical separation. The end of outer spiral supply lead 3 terminates on insulation layer 8 and is electrically connected to ring contact pole 5.

A flexible spiral piece 15 is placed on connector 14 facing the distal end, connecting head 16 of tip contact pole 6 in a mechanically flexible manner and electrically via connector 17 thereof. Spiral piece 15 therefore functions as a joint, thereby enabling the entire end region on distal end 1 to adapt well to curves in the vessel accommodating the electrode device, in particular during introduction.

In the embodiment shown in FIG. 1, tip contact pole 6 is designed as fixing helix 16, the corkscrew-type screw part of which is used to affix the electrode device in bodily tissue in a known manner.

As an alternative to the fixing helix shown, silicone anchors can be provided in the conventional manner.

Although not depicted separately in the drawings, electrode devices having an integrated filter can also comprise a ring contact pole 5 which is not designed as a closed ring. Instead, the electrical contact of the ring contact pole is composed of a structure that comprises e.g. one or more annular segments. The advantage of such a solution is the additional space in the cross section of the electrode e.g. to enable better integration of electrical components.

Figure 2:
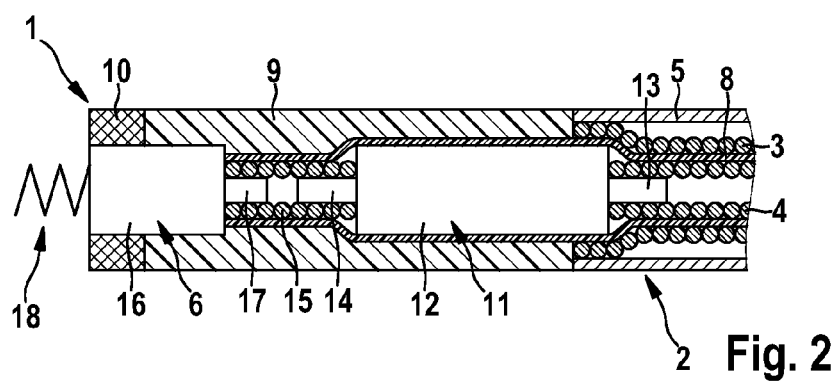

The variant of the electrode device shown in FIG. 2 differs from the embodiment according to FIG. 1 in terms of the positioning of ring contact pole 5 which is offset rearward in the proximal direction and therefore only partially overlaps high-frequency filter 11. Outer supply lead 3 for ring contact pole 5 terminates before high-frequency filter 11 in the proximal direction, and therefore installation space for supply lead 3 does not need to be provided between ring contact pole 5 and filter 11. The entire electrode device can therefore be designed with a smaller diameter.

Figure 3:
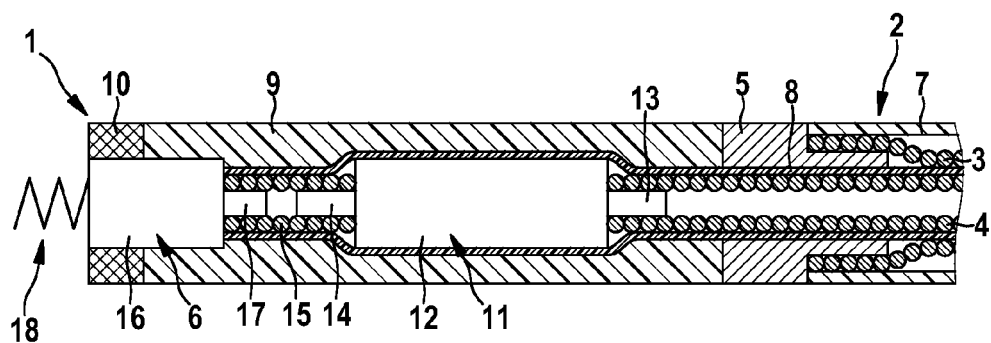

This effect is enhanced further in the embodiment according to FIG. 3 since, in this case, ring contact pole 5 and high-frequency filter 11 do not overlap at all in the longitudinal axial direction. Instead, ring contact pole 5 is located before high-frequency filter 11 in the proximal direction and has an inner diameter d that is smaller than outer diameter D of filter 11. The outer diameter of the ring electrode and, therefore, that of the entire electrode device can be reduced even further. In the embodiments according to FIGS. 2 and 3, insulation sleeve 9 extends partially or completely over insulation layer 8 and high-frequency filter 11 to ring contact pole 5.

Figure 4:
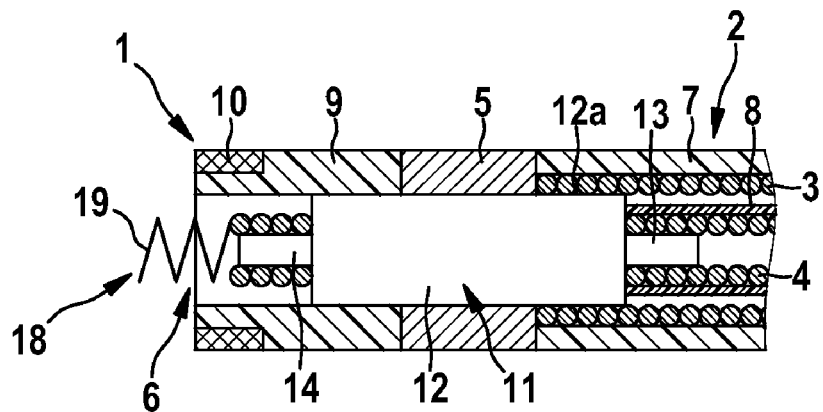

In the embodiment shown in FIG. 4, ring contact pole 5 is situated in the center on high-frequency filter 11 once more, although insulation layer 8 is omitted in this case. The electrical components of high-frequency filter 11 are contacted via outer surface 12a of housing 12 which, together with ring contact pole 5, is connected to outer supply lead 3 and is therefore electrically contacted.

Another difference from the embodiments according to FIGS. 1 to 3 is the design of fixing helix 18. Screw part 19 thereof is placed directly on the distal connector of high-frequency filter 11. Similar to the variants shown in FIGS. 1 to 3, fixing helix 18 is screwed in by rotating entire electrode body 2 about the longitudinal axis thereof.

Figure 5:
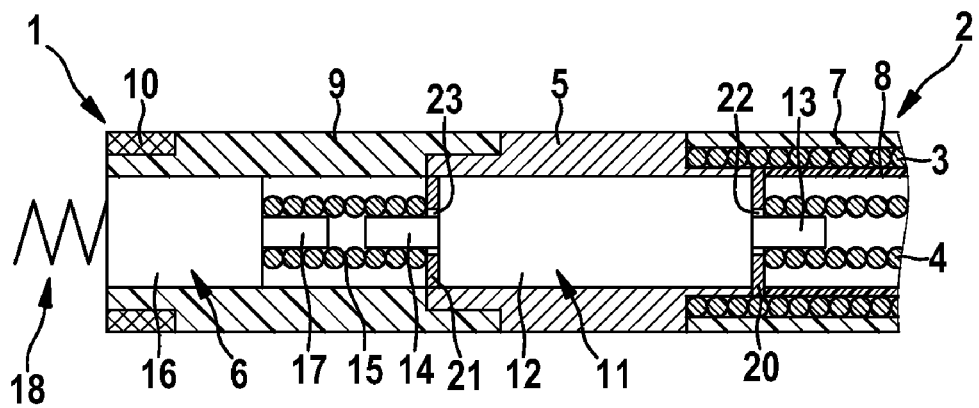

In the embodiment according to FIG. 5, a different concept is implemented for the rotary drive of fixing helix 18, according to which high-frequency filter 11 is supported in bearing washers 20 disposed transversely to the longitudinal axis of electrode body 2 in a rotatable manner since contact pins 13, 14 thereof are situated in bores 22, 23 of bearing washers 20, 21. Inner supply lead 4 is mechanically attached and electrically connected to proximal contact pin 13. Spiral piece 15 connects distal contact pin 14 to connector 17 of head 16 of fixing helix 18 which is rotatably supported in insulating sleeve 9 in this case. In all, fixing helix 18 is actuated by rotating the contact pin (not depicted) on the proximal end of the electrode device. This rotation is transferred via inner supply lead 4 to high-frequency filter 11 and further via spiral piece 15 to fixing helix 18.

Figure 6:
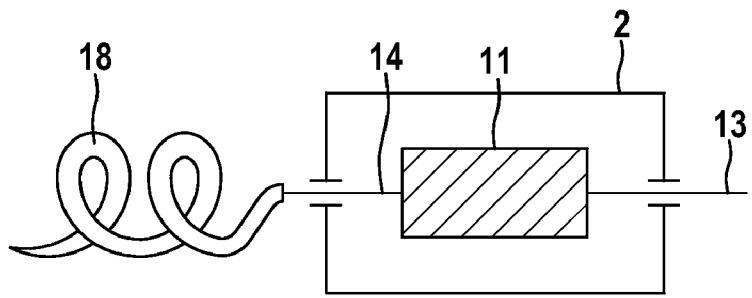
FIGS. 6 to 11 show highly schematicized sectional views of different filter-tip-contact pole configurations.
Figure 7:
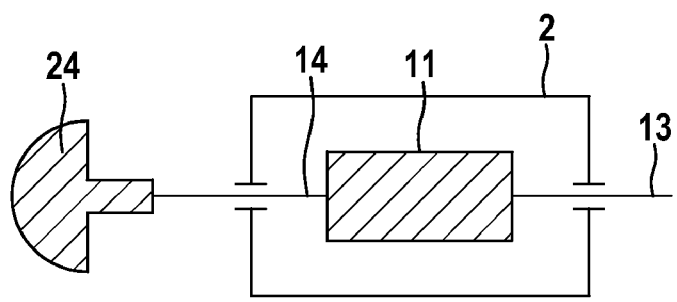
Figure 8:
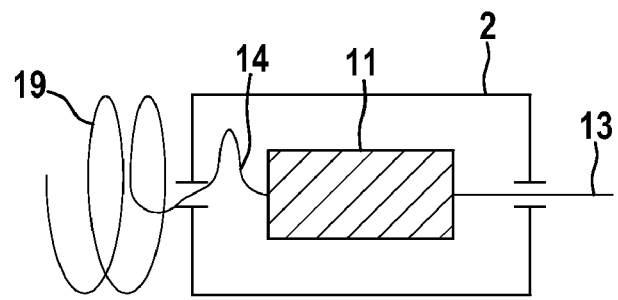

FIGS. 6 to 8 show an overview of various concepts for the embodiments and connection of tip contact poles 6 to high-frequency filter 11. In these Figures, electrode body 2 is depicted in general as a simple box on distal end 1 without showing the design thereof in detail.

FIG. 6 mainly reflects the configuration shown in detail in FIGS. 1 to 5, in which distal contact pin 14 of filter 11 is connected to a fixing helix 18.

In the embodiment shown in FIG. 7, a hemispherical head 24 is used which is disposed on contact pin 14 of the filter.

In the variant according to FIG. 8, screw part 19 is formed directly of distal contact pin 14 of the filter and extends out of electrode body 2.

Figure 9:
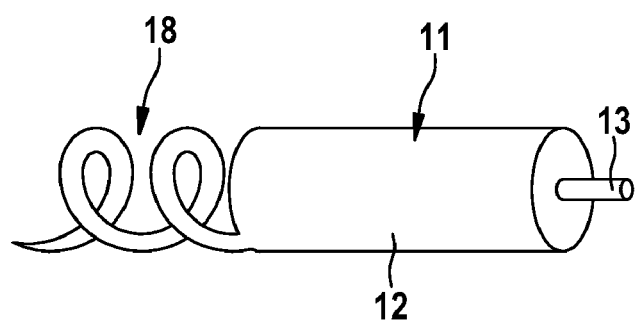

FIG. 9 shows a high-frequency filter 11, housing 12 of which has a fixing helix 18 integrally formed directly thereon, which is then also electrically connected to the components of filter 11.

Figure 10:
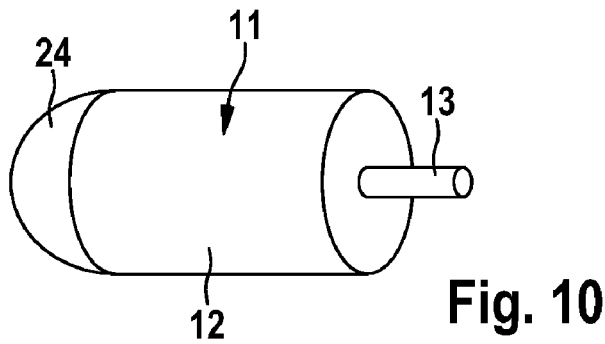
Figure 11:
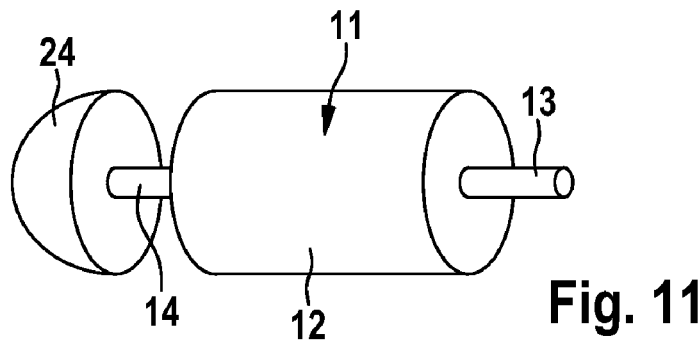

In the embodiment according to FIG. 10, housing 12 of filter 11 comprises a hemispherical head 24 integrally formed directly thereon, which is part of the housing or rests against it. FIG. 11 shows a spacial separation between hemispherical head 24 via contact pin 14.

Hemispherical heads 24 shown in FIGS. 7, 10, and 11 can also be lenticular or conical in design, or have any other shape.

The embodiments of filter 11 shown in conjunction with FIGS. 6 to 11, and the combination thereof with tip-contact poles 6, are used to enable the filter to be better installed in the electrode device and allow it to perform additional functions. The capability of the filter to be integrated is increased compared to conventional filter designs. The electrode device can be designed such that it causes fewer physiological problems since it can be designed to be more flexible, thinner, and have shorter stiff regions. The risk e.g. of perforations of the cardiac muscle are reduced considerably as a result.

Contact poles 5, 6 having any design and the corresponding housing (sections) or parts thereof can be provided with a fractal coating, for example. As an alternative or in addition thereto, the remaining housing regions can be covered with a non-conductive coating. It can be composed of silicone, ceramic, an anorganic layer, a DCL (diamond-like carbon) layer, a plastic such as polyurethane, thermoplastic polyurethane, Parylene, etc. The housing of filter 11 itself can be made of a metal or a metal alloy, preferably stainless steel, platinum, titanium, or a platinum-iridium alloy. It is likewise possible to make the housing of a ceramic or a plastic, wherein these materials can be coated with a conductive material or be conductive themselves. For many filter types it is advantageously to have an additional contact (such as an earth reference or a reference potential, etc.) to the tissue. The electrically conductive housing can establish this contact. Such a contact is unwanted for other filter types, although a metallically conductive shield may be advantageous (or only due to mechanical strength, heat dissipation, etc.). The non-conductive/non-conductively coated housing is therefore preferable in such cases.

In other cases, electrical contact is desired, although not at all frequencies, and mainly not with direct current. The insulating layer is therefore used as a dielectric between the metallic housing and the tissue. Together they form a capacitor.

FIGS. 12 to 15 show alternative designs of high-frequency filter 11, of the type that is also suitable for installation in electrodes for a cardiac pacemaker, defibrillator, neurostimulator or similar active medical implants. Housings of aforementioned filters are typically composed of solid metal parts, and expensive ceramic components are usually used to form insulation between housing and electrical components. The sealing of the housing is very elaborate, problematic, and therefore cost-intensive. The concepts shown in FIGS. 12 to 15 make it possible to create a simply designed seal against fluids, thereby enabling high-frequency filter 11 to be realized in a cost-favorable manner. Highly diverse electrical components can be embedded easily and in a variable manner since the housing is created mainly by providing a coating applied by injection molding, possibly including various pre- and post-handling steps.

Figure 12:
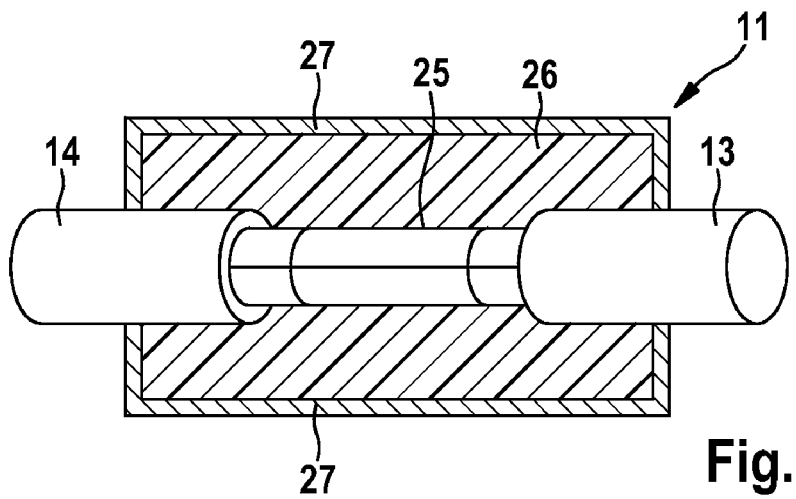
FIGS. 12 to 19 show highly schematicized depictions of high-frequency filters in various embodiments.

In detail, FIG. 12 shows contact pins 13, 14 of filter 11, which are interspaced collinearly and between which one or more electrical components 25 are interconnected accordingly and are therefore connected. The ends of contact pins 13, 14 are left exposed and this entire assembly is enclosed in a plastic body 26 applied by injection molding, which ensures that components 25 are sealed and electrically insulated.

If necessary, filter 11 produced in this manner can also be provided with a coating 27 which can be composed e.g. of a plastic, a ceramic, or another type of anorganic layer. Such a functional coating 27 is used to adapt the surface properties to particular usage conditions; for example, coating 27 can provide mechanical stabilization or form a vapor barrier.

Figure 13:
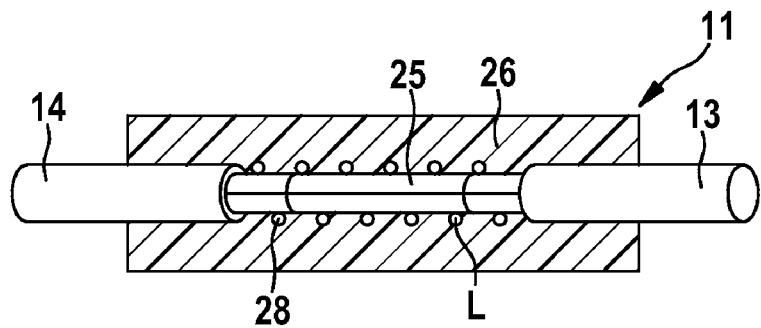

The embodiment depicted in FIG. 13 differs from that shown in FIG. 12 in that a wire-wound coil 28, which can provide inductance L of the high-frequency filter, is also wound around electrical components 25 between contact pins 13, 14.

Figure 14:
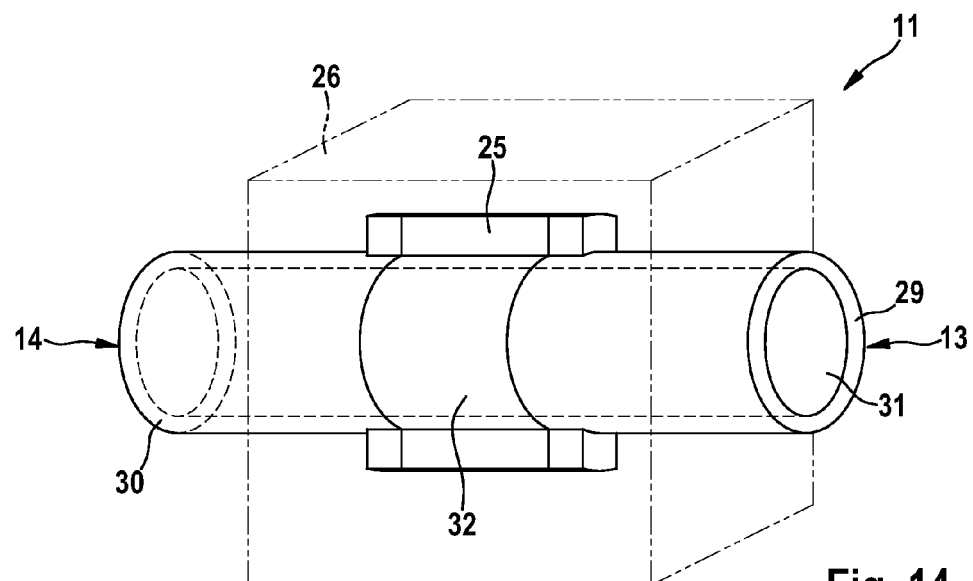

To provide an electrode device with a high-frequency filter 11 and simultaneously enable the use of a guide wire, FIG. 14 shows an embodiment in which contact pins 13, 14 are designed as conductive tubes 29, 30, lumina 31 of which align with a corresponding passage 32 in plastic body 26 that forms filter housing 12. A guide wire, mandrel, or the like can then pass through lumen 31 and passage 32. As shown clearly in FIG. 14, electrical components 25 are embedded such that they are offset laterally relative to passage 32.

Figure 15:
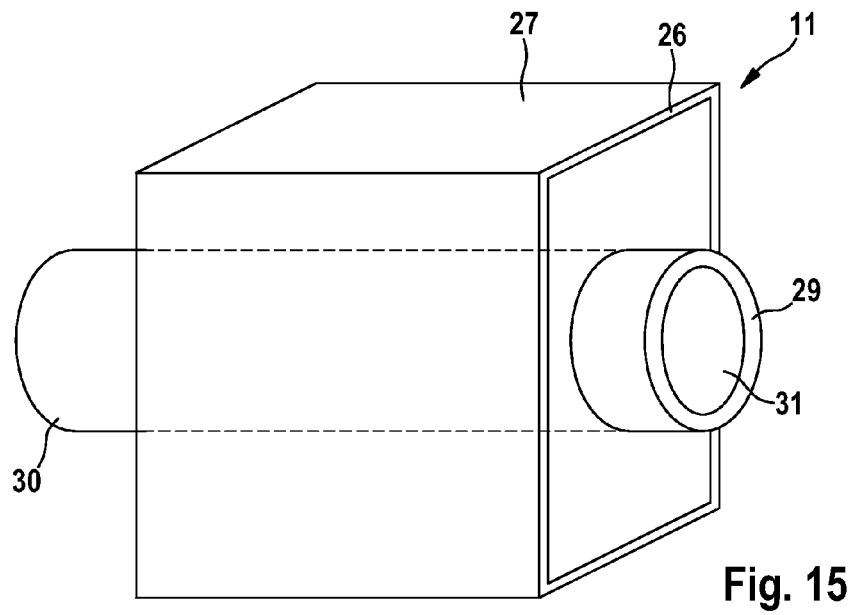

FIG. 15 shows another outer view of the filter depicted in FIG. 14, in which case as well a coating 27 of metal, various plastics or anorganic or organic compounds depending on the desired functionality is applied to the housing.

Electrical contact pins 13, 14 or tubes 29, 30 can be composed of stainless steel, platinum, platinum-iridium alloy, or titanium. They may also be provided with one or more bores, grooves, engravings, or recesses to increase the mechanical strength of filter 11 after the coating is applied by injection molding, thereby stabilizing it overall.

FIGS. 16 to 21 show embodiments of a high-frequency filter 11 that require no contact pins 13, 14, and the housing of which can therefore be sealed in a simple manner. In the case of the above-described variants of filter 11, contact pins 13, 14 increase the overall size of filter 11, and additional passages must be insulated or sealed off.

Figure 16:
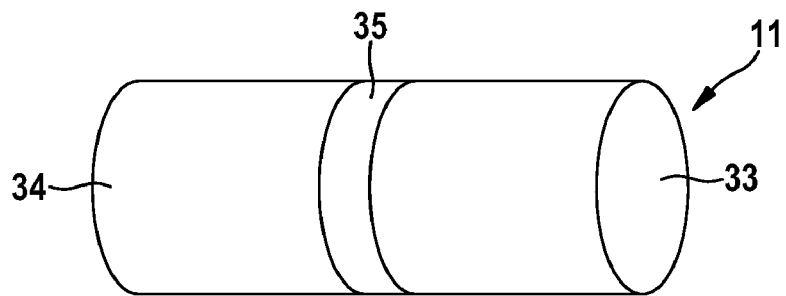
Figure 17:
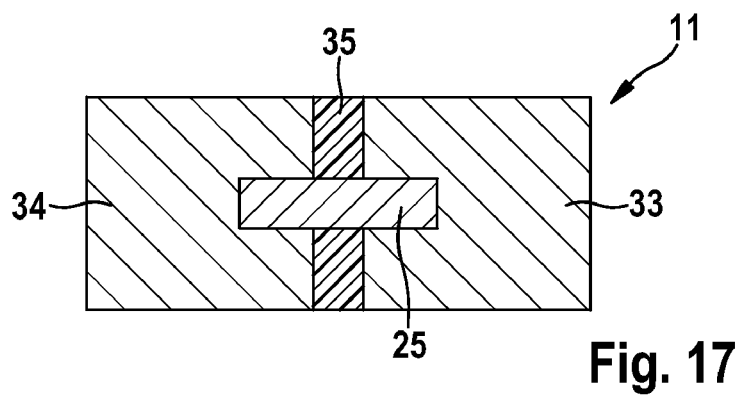

As made clear in the view according to FIG. 16 and the schematic sectional view according to FIG. 17, the contact pins are formed by two contact caps 33, 34 which are insulated from one another, and which are mechanically connected and electrically insulated by an insulator insert 35. The two "semi-barrels" formed by contact caps 33, 34 are connected in a water-tight manner, and two electrically separated regions result.

Figure 18:
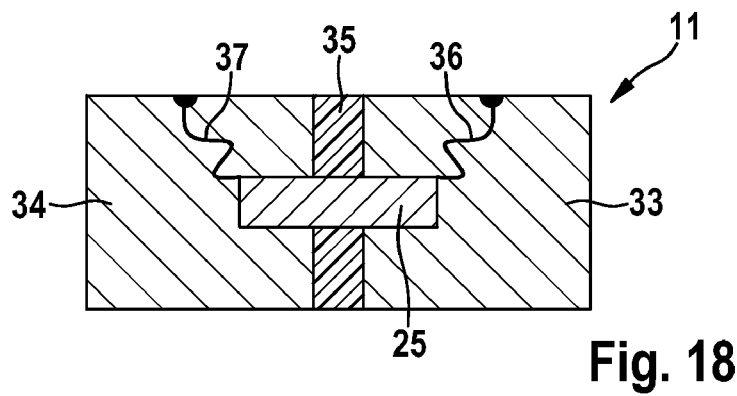

Electrical components 25 are arranged in insulator insert 35 in an appropriate configuration so that they have e.g. a high-pass, low-pass, bandpass, or band-stop behavior. Electrical components 25 are electrically connected to the inside of contact caps 33 and 34. As indicated in FIG. 18, this takes place via appropriate connecting lines 36, 37 which are formed by typical wires, litz wires, or wire cables, and can be welded, crimped, or lased to the inside of contact caps 33, 34. An inductively or capacitively coupling connection of the connectors is also feasible.

The embodiment of high-frequency filter 11 as a barrel filter described results in a shortening of the overall size and increases safety by reducing connection points. When installed in an electrode device, the region reinforced by the filter therefore also becomes shorter, thereby improving the properties of the electrode device in vivo mainly in respect to the implantability, risk of perforation, and long-term stability.

Figure 19:
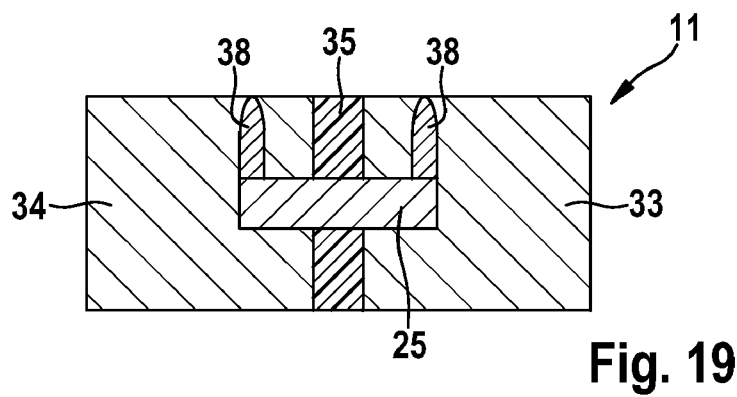

As shown in FIG. 19, components 25 can also be electrically contacted via sliding contacts 38 or corresponding contact springs which have electrical contact with the inner side of contact caps 33 and 34.

Figure 20:
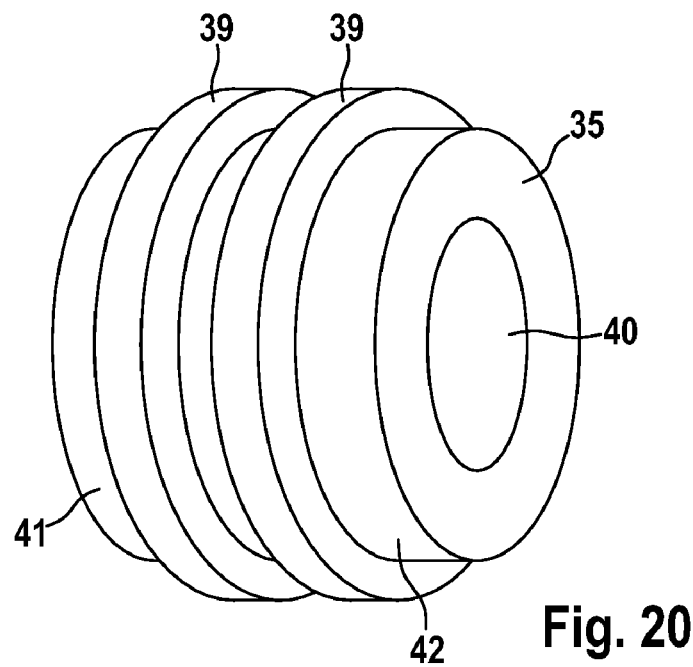
FIGS. 20 and 21 show partial depictions of high-frequency filters.

FIG. 20 shows a special embodiment of insulator insert 35, on which welding discs 39 composed of metal have been placed. They extend radially beyond the jacket wall of cylindrical insulator insert 35 and are used to connect contact caps 33, 34 by welding. Furthermore, insulator insert 35 has a passage coaxially in the center, similar to a tube, in the form of a bore or the like, as a recess for components 25.

Figure 21:
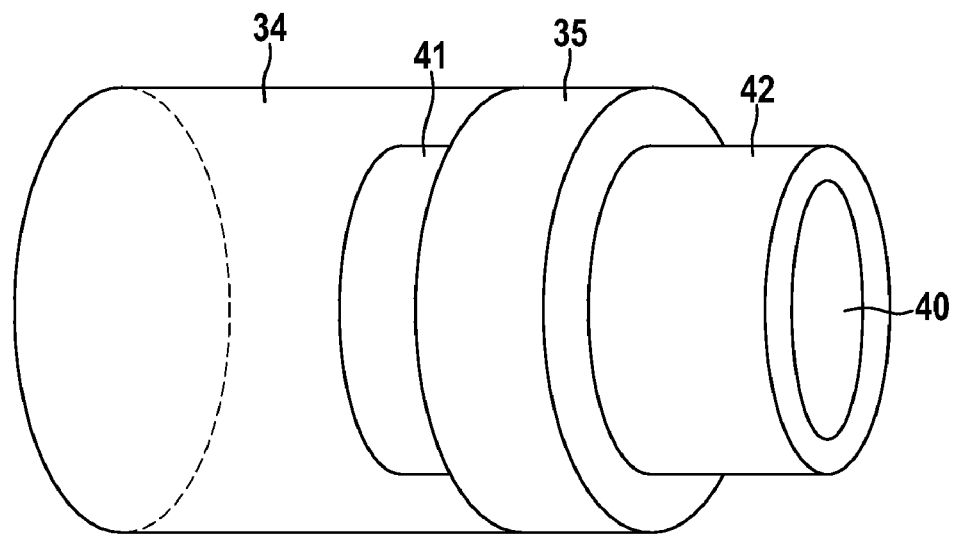

Insulator insert 35, as an insulating intermediate piece, can be composed e.g. of ceramic or plastic, onto corresponding projections 41, 42 of which the contact caps—left contact cap 34 is shown in FIG. 21—can be slid and fastened to insulator insert 35 by welding, soldering, bonding, crimping, or the like.

Instead of metal, the two semi-barrels of contact caps 33, 34 can also be made of a plastic, a conductive plastic, a ceramic, or another non-conductor. They must then be coated entirely or partially with a conductive material.

Finally, FIGS. 22 to 31 show the integral design of a high-frequency filter 11 with direct embedding in a tip contact pole 6. To integrate filter 11 for the tip supply lead of the electrode device, the filter is accommodated e.g. between the fixing helix and the inner supply lead of the tip contact pole in a so-called pin unit 43. The coil and the filter can be integrated using discrete components such as SMD components. Integration using other methods is also possible. The connections between the electrode supply leads and the filter itself can be composed of various materials, e.g. metallic materials, metallic materials having a partial insulating coating, non-conductive materials having integrated, applied electrical leads, or suitable combinations thereof. In other words, the function is attained not by using SMD components, for instance, but rather by specifically joining materials having suitable properties. For instance, a sandwich composed of conductive material, non-conductive (particularly dielectric) material, conductive material form a capacitor in the order of this listing. Another example: an oxidized metal can impart semiconductive properties (diode) at the metal/metal oxide boundary layer.

Figure 22:
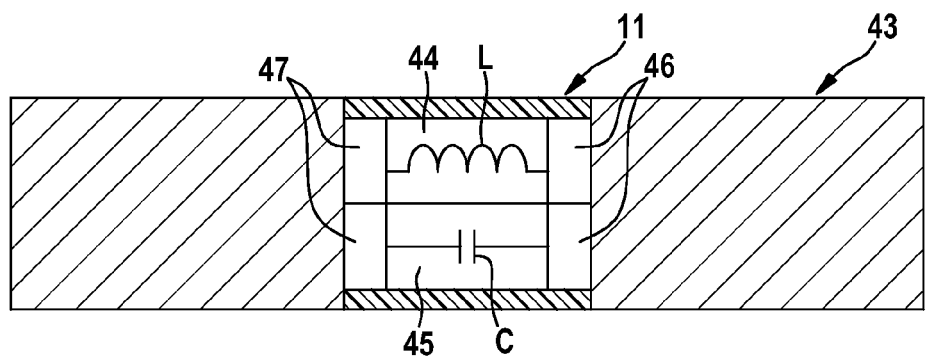

Various specific possibilities for integration are explained below. For example, FIG. 22 shows a component as pin unit 43, in which a filter composed of two SMD components 44, 45 in the form of inductance L and capacitance C connected in parallel is realized. The design of SMD components 44, 45 need not be identical. They are integrated completely in the pin unit, which can therefore be manufactured isodiametrically. Connectors 46, 47 to the left and right are composed of conductive material.

Figure 23:
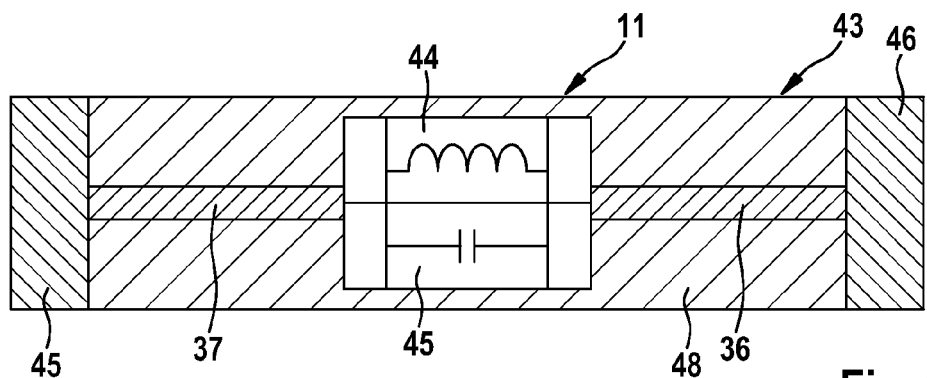

As shown in FIG. 23, pin unit 43 can also be composed of a body 48 of dielectric material, which has corresponding connecting lines 36, 37 between SMD components 44, 45, which form the filter components, and connectors 46, 47. This design places less of a demand on the filter components since they are embedded in an homogeneous material.

Figure 24:
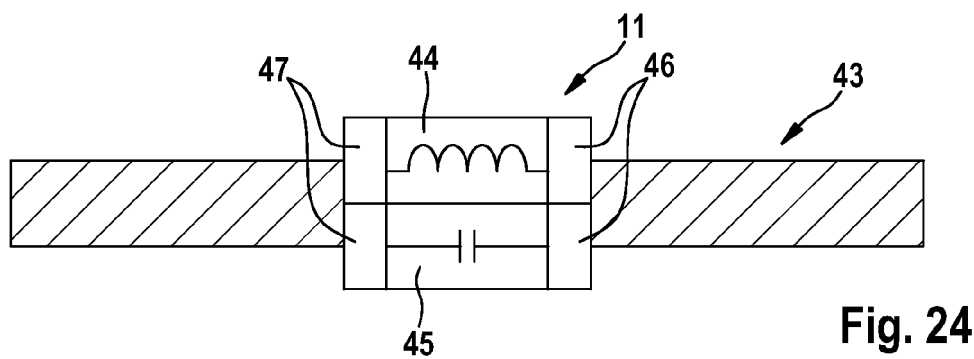

In the embodiment shown in FIG. 24, high-frequency filter 11 and SMD components 44, 45 thereof are integrated in a body 48 having a relatively thin structure. The installation between two conductive elements is omitted in this drawing. Entire pin unit 43 is therefore not necessarily isodiametrical. As described with reference to FIG. 23, this embodiment can also be composed of dielectric material having suitable lead structures.

Figure 25:
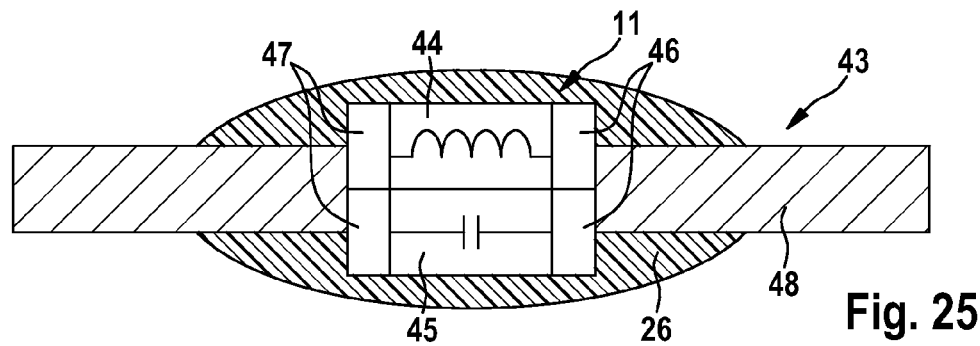

To separate high-frequency filter 11 itself from the surroundings, it is enclosed in a plastic body 26 applied by injection molding, a coating, a housing, or a similar measure, as shown in FIG. 25.

Figure 26:
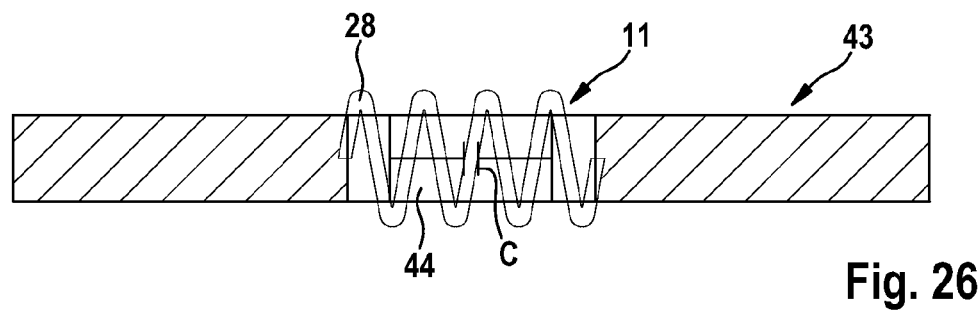
Figure 27:
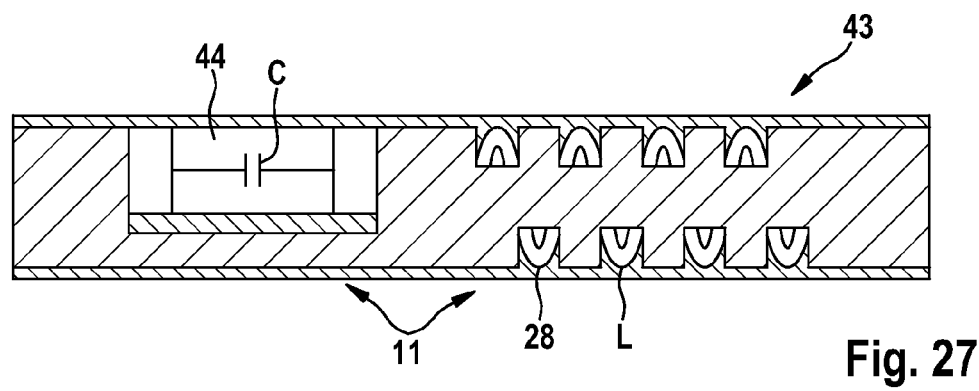

A further miniaturization of pin unit 43 is attained using the embodiment shown in FIG. 26. In that case, wire-wound coil 28 of high-frequency filter 11 is placed around SMD component 44 which is designed as capacitor C. The amount of space required is therefore markedly reduced compared to the above-described embodiments according to FIGS. 22 to 25.

Figure 28:
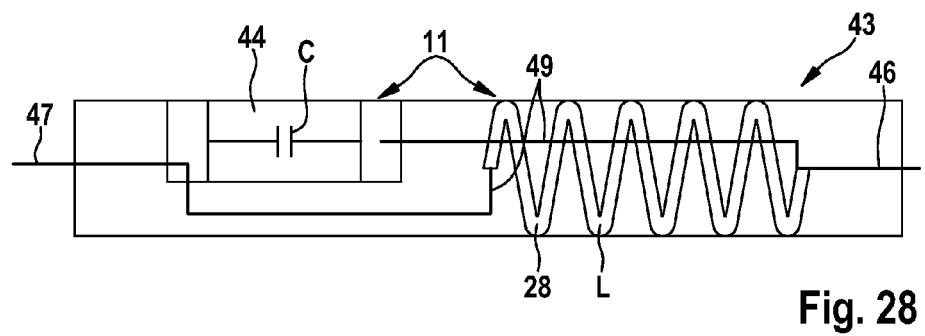

In the embodiment of pin unit 43 depicted in FIG. 28, coil 28 and SMD component 44 for capacitance C are installed mechanically one behind the other, wherein interconnection 49 emphasized using solid lines is parallel. The pin unit can be isodiametric in design and comprise appropriate connectors 46, 47 on the ends thereof. In the interior of the component, capacitance C is installed as capacitor SMD component 44, and inductance L is installed as wire-wound coil. In FIG. 28, the supporting structure of the body of the pin unit is omitted for clarity.

Figure 29:
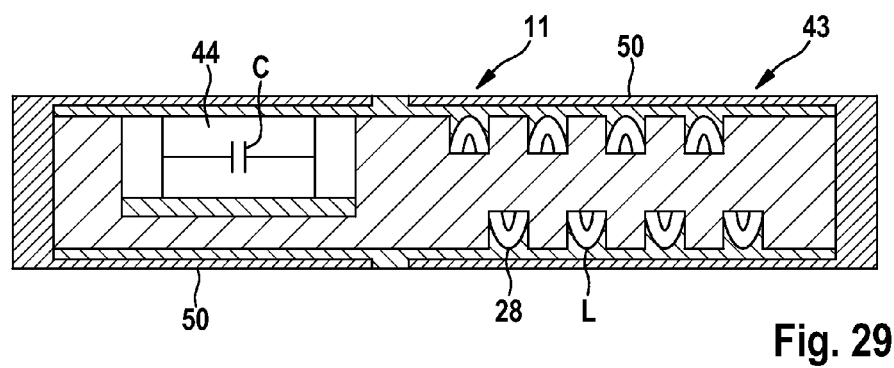
Figure 30:
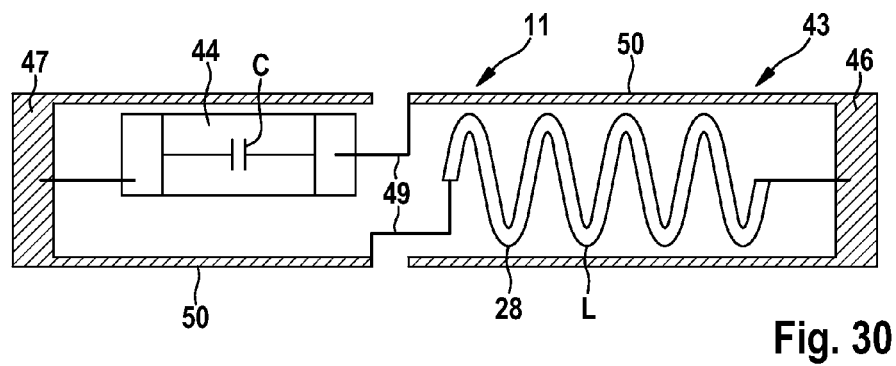

Such a supporting structure is shown in FIG. 29. Furthermore, this embodiment comprises a metallization 50 which extends over wide subregions of pin unit 43 on the outer side thereof. The contacting of the components takes place via metallization 50, namely that of wire-wound coil 28 and capacitor SMD component 44, as shown in FIG. 30. Interconnection 49 can therefore be designed with shorter paths in the interior.

Finally, FIG. 31 shows an embodiment in which pin unit 43 has a larger diameter on the distal end thereof. Screw part 19 of fixing helix 18 of tip contact pole 6 formed in this manner is fastened on shoulder 51 formed as a result. High-frequency filter 11 with SMD components 44, 45 thereof are integrated in the region of shoulder 51. The integration of a bandstop filter having an SMD component 44 as capacitance C and a component 45 as inductance L is shown in FIG. 31 as an example. Filter 11 is electrically connected via stop ring 52 on proximal end 53 of shaft 54 of pin unit 43 via an embedded connecting line 36.

The above-described concepts in combination with FIGS. 22 to 31 are likewise possible using coils that are wound, planar, or integrated in LTCC.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE CHARACTERS

1 Distal end
2 Electrode body
3 Outer supply lead
4 Inner supply lead
5 Ring contact pole
6 Tip contact pole
7 Tube
8 Insulation layer
9 Insulation sleeve
10 Steroid collar
11 High-frequency filter
12 Housing 12a Outer surface
13 Contact pin
14 Contact pin
15 Spiral piece
16 Head
17 Connection
18 Fixing helix
19 Screw part
20 Bearing washer
21 Bearing washer
22 Bore in the bearing
23 Bore in the bearing
24 Hemispherical head
25 Electrical components
26 Plastic body
27 Coating
28 Wire-wound coil
29 Tube
30 Tube
31 Lumen
32 Passage
33 Contact cap
34 Contact cap
35 Insulator insert
36 Connecting line
37 Connecting line
38 Sliding contact
39 Welding disc
40 Passage
41 Shoulder
42 Shoulder
43 Pin unit
44 SMD component
45 SMD component
46 Connection
47 Connection
48 Body
49 Interconnection
50 Metallization
51 Shoulder
52 Stop ring
53 Proximal end (FIG. 31)
54 Shaft
d Inner diameter of 5
D Outer diameter of 11

What is claimed is:

1. An electrode device for active medical implants, comprising:
 an elongated electrode body having a proximal end and a distal end;
 a tip contact pole on the distal end;
 at least one ring contact pole proximal to the distal end;
 electrical supply leads to the tip contact pole and the at least one ring contact pole;

a high-frequency filter proximal to the distal end, which has electrical contact with the tip contact pole and is connected to the respective electrical supply lead thereof; and, wherein the at least one ring contact pole is disposed in front of the high-frequency filter in the proximal direction such that the at least one ring contact pole and the high-frequency filter do not overlap axially, and the inner diameter (d) of the at least one ring contact pole, is smaller than the outer diameter (D) of the high-frequency filter.

2. The electrode device according to claim 1, wherein the high-frequency filter is positioned at least partially within the at least one ring contact pole in a radially overlapping manner.

3. The electrode device according to claim 2, further comprising a spiral supply lead for the at least one ring contact pole that terminates in front of the high-frequency filter in the proximal direction.

4. The electrode device according to claim 2, further comprising an outer supply lead for the at least one ring contact pole that simultaneously has electrical contact with an outer surface of a housing of the high-frequency filter.

5. The electrode device according to claim 1, wherein the high-frequency filter is connected mechanically and electrically to the tip contact pole by a flexible spiral piece.

6. The electrode device according to claim 1, wherein the tip contact pole is selected from the following components:
a head having an electrically active fixing screw,
a lenticular, conical, or hemispherical head,
an elongated contact pin configured as a fixing screw of the high-frequency filter, or
a projection of a housing of the high-frequency filter.

7. The electrode device according to claim 1, wherein the high-frequency filter, together with the tip contact pole configured as electrically active fixing screw, is supported in the electrode device, in particular within the at least one ring contact pole such that it can rotate about a longitudinal axis of the electrode device.

8. The electrode device according to claim 7, wherein the high-frequency filter comprises contact pins that are rotatably supported in bores of bearing washers and are rotationally driven by the electrical supply lead of the tip contact pole.

9. The electrode device according to claim 1, wherein the high-frequency filter comprises electrical contact pins having miniature electronic components connected therebetween, wherein contact pins and miniature components are all enclosed in a bonded manner in a filter housing applied by injection molding.

10. The electrode device according to claim 9, wherein the outer side of the filter housing is provided with a functional coating.

11. The electrode device according to claim 9, wherein the electrical contact pins are each configured as a tube, the lumina of which align with a passage in the filter housing as passage for a guide wire configured to implant the electrode device.

12. The electrode device according to claim 10, wherein the electrical contact pins are each configured as a tube, having a lumina of which aligns with a passage in the filter housing as passage for a guide wire configured to implant the electrode device.

13. The electrode device according to claim 1, wherein the high-frequency filter comprises electrical contact pins configured as contact caps insulated from one another and facing one another, in the interior of which electrical components of the high-frequency filter are disposed.

14. The electrode device according to claim 13, wherein connections of the electrical components have electrical contact with an inner side of the contact caps, via sliding contacts or contact springs.

15. The electrode device according to claim 1, wherein the high-frequency filter is integrated directly in the tip contact pole.

16. An electrode device for active medical implants, comprising:
an elongated electrode body having a proximal end and a distal end;
a tip contact pole on the distal end;
at least one ring contact pole proximal to the distal end;
electrical supply leads to the tip contact pole and the at least one ring contact pole; and,
a high-frequency filter proximal to the distal end, which has electrical contact with the tip contact pole and is connected to the respective electrical supply lead thereof; and,
wherein the high-frequency filter is connected mechanically and electrically to the tip contact pole by a flexible spiral piece.

17. An electrode device for active medical implants, comprising:
an elongated electrode body having a proximal end and a distal end;
a tip contact pole on the distal end;
at least one ring contact pole proximal to the distal end;
electrical supply leads to the tip contact pole and the at least one ring contact pole;
a high-frequency filter proximal to the distal end, which has electrical contact with the tip contact pole and is connected to the respective electrical supply lead thereof;
wherein the high-frequency filter, together with the tip contact pole configured as electrically active fixing screw, is supported in the electrode device, in particular within the at least one ring contact pole such that it can rotate about a longitudinal axis of the electrode device; and,
wherein the high-frequency filter comprises contact pins that are rotatably supported in bores of bearing washers and are rotationally driven by the electrical supply lead of the tip contact pole.

18. An electrode device for active medical implants, comprising:
an elongated electrode body having a proximal end and a distal end;
a tip contact pole on the distal end;
at least one ring contact pole proximal to the distal end;
electrical supply leads to the tip contact pole and the at least one ring contact pole; and,
a high-frequency filter proximal to the distal end, which has electrical contact with the tip contact pole and is connected to the respective electrical supply lead thereof; and,
wherein the high-frequency filter comprises electrical contact pins having miniature electronic components connected therebetween, wherein contact pins and miniature components are all enclosed in a bonded manner in a filter housing applied by injection molding.

19. The electrode device according to claim 18, wherein the outer side of the filter housing is provided with a functional coating.

20. The electrode device according to claim 18, wherein the electrical contact pins are each configured as a tube, the lumina of which align with a passage in the filter housing as passage for a guide wire configured to implant the electrode device.

* * * * *